United States Patent
Casey et al.

(10) Patent No.: US 10,029,053 B2
(45) Date of Patent: Jul. 24, 2018

(54) NEBULIZER

(71) Applicant: Stamford Devices Limited, Galway (IE)

(72) Inventors: Michael Casey, CorrnaMona (IE); Joseph Grehan, Gort (IE); Kieran Hyland, Galway (IE); John Power, Moycullen (IE)

(73) Assignee: STAMFORD DEVICES LTD., Galway (IE)

( * ) Notice: Subject to any disclaimer, the term of this patent is extended or adjusted under 35 U.S.C. 154(b) by 1156 days.

(21) Appl. No.: 13/870,376

(22) Filed: Apr. 25, 2013

(65) Prior Publication Data
US 2013/0291859 A1 Nov. 7, 2013

Related U.S. Application Data

(60) Provisional application No. 61/642,284, filed on May 3, 2012.

(51) Int. Cl.
*A61M 11/00* (2006.01)
*B05B 17/06* (2006.01)
(Continued)

(52) U.S. Cl.
CPC ........... *A61M 11/00* (2013.01); *A61M 11/005* (2013.01); *B05B 12/00* (2013.01);
(Continued)

(58) Field of Classification Search
CPC .... A61B 2562/0219; A61B 2562/0271; A61B 5/1117; A61B 5/681; A61B 5/6831;
(Continued)

(56) References Cited

U.S. PATENT DOCUMENTS 4,659,161 A * 4/1987 Holcomb ............... H01R 31/02
439/490
5,551,416 A 9/1996 Stimpson et al.
(Continued)

FOREIGN PATENT DOCUMENTS

| CN | 2724758 Y | 9/2005 |
|---|---|---|
| CN | 201303250 | 9/2009 |

(Continued)

OTHER PUBLICATIONS

Extended European Search Report for 12166525.1-2320 dated Jul. 12, 2012 (8 pages).
(Continued)

*Primary Examiner* — Annette Dixon
(74) *Attorney, Agent, or Firm* — Bookoff McAndrews, PLLC

(57) ABSTRACT

A nebulizer comprises a controller linked at its output to a nebulizer head, and at its input to a USB cable and USB plug for connection to a host system. The link between the USB plug and the controller is a USB cable with power and data channels. The controller comprises a boost circuit, a microcontroller 11, and a drive circuit. The latter provides power and control signals via a cable and proprietary plug to the nebulizer head. These signals provide power and control for a vibrating membrane receiving a liquid to be aerosolized. The controller has a housing with LED status lamps, and an ON/OFF button. The controller can be controlled via a host, either locally or remotely.

17 Claims, 3 Drawing Sheets

(51) Int. Cl.
    *B05B 17/00* (2006.01)
    *B05B 12/00* (2018.01)
(52) U.S. Cl.
    CPC ... *B05B 17/0646* (2013.01); *A61M 2205/502* (2013.01); *A61M 2205/52* (2013.01); *A61M 2205/587* (2013.01); *A61M 2205/70* (2013.01)
(58) Field of Classification Search
    CPC .............. A61M 11/003; A61M 11/005; A61M 11/042; A61M 15/00; A61M 16/0003; A61M 2016/0021; A61M 2016/0027; A61M 2016/003; A61M 2205/332; A61M 2205/3334; A61M 2205/3368; A61M 2205/3375; A61M 2205/50; A61M 2205/82; A61M 2205/8206; A61M 2205/8237; A61M 2210/0612; A61M 5/16886; G01P 13/006; G01P 5/10; G01P 5/12; G08B 21/0446; Y10T 29/49117; Y10T 29/49128
    USPC ........................................ 128/200.16, 203.12
    See application file for complete search history.

(56) References Cited

U.S. PATENT DOCUMENTS

| | | | |
|---|---|---|---|
| 6,615,825 B2 | 9/2003 | Stenzler | |
| 9,060,715 B2* | 6/2015 | Schipper | A61B 5/1117 |
| 2002/0038394 A1* | 3/2002 | Liang | G06F 1/266 |
| | | | 710/62 |
| 2003/0150451 A1* | 8/2003 | Shayan | A61M 11/041 |
| | | | 128/203.12 |
| 2005/0011514 A1 | 1/2005 | Power et al. | |
| 2005/0284470 A1 | 12/2005 | Wei et al. | |
| 2006/0258215 A1 | 11/2006 | Lai et al. | |
| 2008/0143185 A1* | 6/2008 | Ingles | G06F 1/266 |
| | | | 307/44 |
| 2008/0149096 A1 | 6/2008 | Power | |
| 2008/0244107 A1* | 10/2008 | Uno | G06F 9/4411 |
| | | | 710/15 |
| 2009/0058635 A1* | 3/2009 | LaLonde | A61N 1/37282 |
| | | | 340/539.11 |
| 2009/0063187 A1* | 3/2009 | Johnson | A61B 5/0022 |
| | | | 705/2 |
| 2009/0110148 A1* | 4/2009 | Zhang | A61B 5/0002 |
| | | | 378/95 |
| 2009/0113093 A1* | 4/2009 | Chen | H01R 31/06 |
| | | | 710/74 |
| 2009/0151718 A1* | 6/2009 | Hunter | A61M 16/209 |
| | | | 128/203.12 |
| 2009/0156952 A1* | 6/2009 | Hunter | A61M 16/209 |
| | | | 600/538 |
| 2010/0056956 A1* | 3/2010 | Dufresne | A61B 7/04 |
| | | | 600/586 |
| 2010/0067197 A1* | 3/2010 | Guccione | G06F 1/26 |
| | | | 361/728 |
| 2010/0321939 A1* | 12/2010 | Patel | F21S 6/002 |
| | | | 362/253 |
| 2011/0036346 A1 | 2/2011 | Cohen et al. | |
| 2011/0253139 A1* | 10/2011 | Guthrie | A61M 15/009 |
| | | | 128/203.14 |
| 2012/0003854 A1* | 1/2012 | He | H01R 13/70 |
| | | | 439/188 |
| 2012/0099629 A1* | 4/2012 | Faulkner | H04L 12/26 |
| | | | 375/222 |
| 2012/0111970 A1* | 5/2012 | Hogan | B05B 17/0646 |
| | | | 239/102.2 |
| 2012/0272952 A1* | 11/2012 | Hsiao | A61M 11/005 |
| | | | 128/200.16 |
| 2012/0303331 A1* | 11/2012 | Niemczak | G06F 19/3406 |
| | | | 702/198 |
| 2013/0071808 A1* | 3/2013 | Van der Laan | A61B 1/24 |
| | | | 433/29 |

FOREIGN PATENT DOCUMENTS

| | | |
|---|---|---|
| CN | 201781983 | 4/2011 |
| DE | 19934582 A1 | 1/2001 |
| EP | 0831384 A1 | 3/1998 |
| EP | 1184083 A1 | 3/2002 |
| EP | 2067497 A1 | 6/2009 |
| EP | 2072144 A1 | 6/2009 |
| WO | WO 2010/035252 A2 | 4/2010 |
| WO | WO-2012026963 A2 | 3/2012 |
| WO | WO 2012/046220 A2 | 4/2012 |

OTHER PUBLICATIONS

International Search Report for PCT/EP2013/058646, dated Oct. 21, 2013 (5 pages).

* cited by examiner

NEBULIZER

CROSS REFERENCE TO RELATED APPLICATIONS

The present application claims the benefit of U.S. provisional application Ser. No. 61/642,284, filed on May 3, 2012, the contents of which are herein incorporated by reference in their entirety.

INTRODUCTION

Field of the Invention

The invention relates to a nebulizer, and more particularly to power supply and control of aerosol generation in nebulizers.

Prior Art Discussion

Aerosol delivery systems can aerosolise a broad range of liquids across a particle range 1-50 μm MMAD. Such systems have an aperture plate with holes of pre-determined size and which is coupled with a vibrational mechanism powered by a piezo. The aperture plate is vibrated at a frequency of typically 120 to 150 kHz and this action causes the liquid to break surface tension and it creates an aerosol plume as droplets pass through the aperture plate. An example is described in WO2010035252 (Stamford Devices Ltd).

WO2012/026963 (Rubin) describes an aerosol delivery system having an integral USB plug.

SUMMARY OF THE INVENTION

According to the invention, there is provided a nebulizer comprising a nebulizer head for generating an aerosol, a controller for delivering power and control signals to the nebulizer head, and a standard universal bus for delivering power and control signals to the controller,
  wherein the standard universal bus comprises a universal plug and a universal cable extending from said plug to the controller,
  wherein the controller is linked by a cable and a plug to the nebulizer head; and
  wherein the controller comprises a voltage boost circuit linked at its input with the universal bus, a processor, and a drive circuit for delivering power to the nebulizer head under control of the processor.

In one embodiment, the universal bus is a USB bus, and wherein total power requirement of the controller and of the nebulizer head falls within the power specification of the standard USB protocol.

In one embodiment, the controller provides to the nebulizer head no more than 500 mA at nominal 5V.

In one embodiment, the drive circuit is adapted to generate a waveform in the range of 120 kHz and 150 kHz.

In one embodiment, the boost circuit is adapted to generate a voltage supply for the processor and the drive circuit. Preferably, the voltage level is 12 V.

In one embodiment, the processor is adapted to upload the following information to a host via the universal bus:
  power consumption, and/or
  wet/dry state of the nebulizer head, and/or
  nebulizer disconnect status, and/or
  cable disconnect status, and/or
  error or fault states, and/or
  nebulization duration and time of nebulization.

In another embodiment, the controller is adapted to receive the following signals from a host via the universal bus and to use them to generate nebulizer head drive signals:
  nebulization start/stop, and/or
  nebulization time, and/or
  nebulization flow rate, and/or
  nebulization pulse rate, and/or
  inspiratory/expiratory signal to enable phased nebulization In another aspect, the invention provides a nebulizer system comprising a nebulizer as defined above in any embodiment, and a host system adapted to provide control signals to the controller via said bus.

In one embodiment, the host system is adapted to provide the control signals according to a patient dosing regime.

In one embodiment, the host system includes a component adapted to communicate with a remote server for download of control instructions and/or upload of nebulizer data.

In one embodiment, the host system includes a portable device such as a smartphone or tablet computer.

DETAILED DESCRIPTION OF THE INVENTION

The invention will be more clearly understood from the following description of some embodiments thereof, given by way of example only with reference to the accompanying drawings in which:—

DESCRIPTION OF THE EMBODIMENTS

Figure 1:
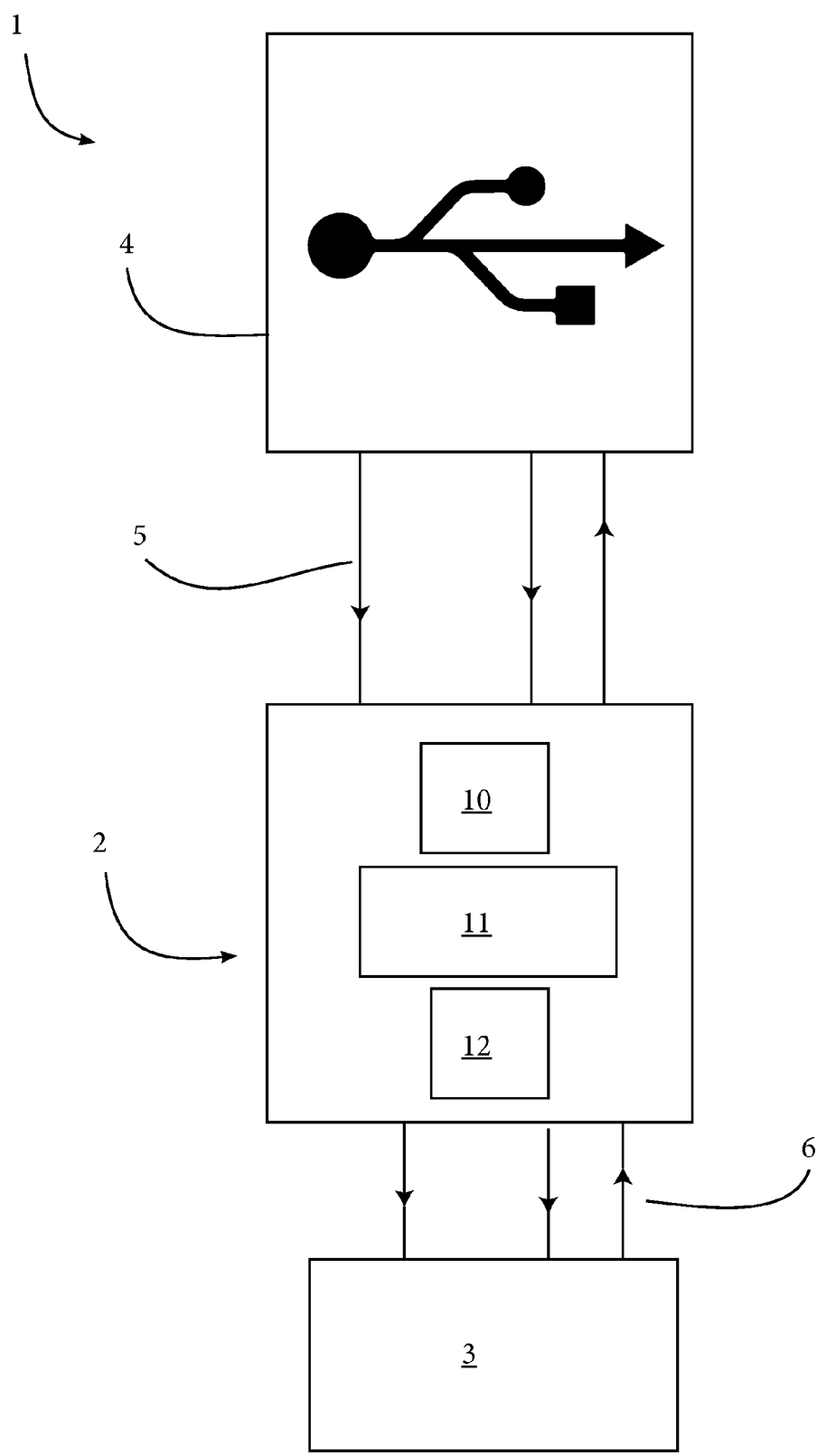
FIG. 1 is a block diagram illustrating architecture of a nebulizer of the invention.
Figure 2:
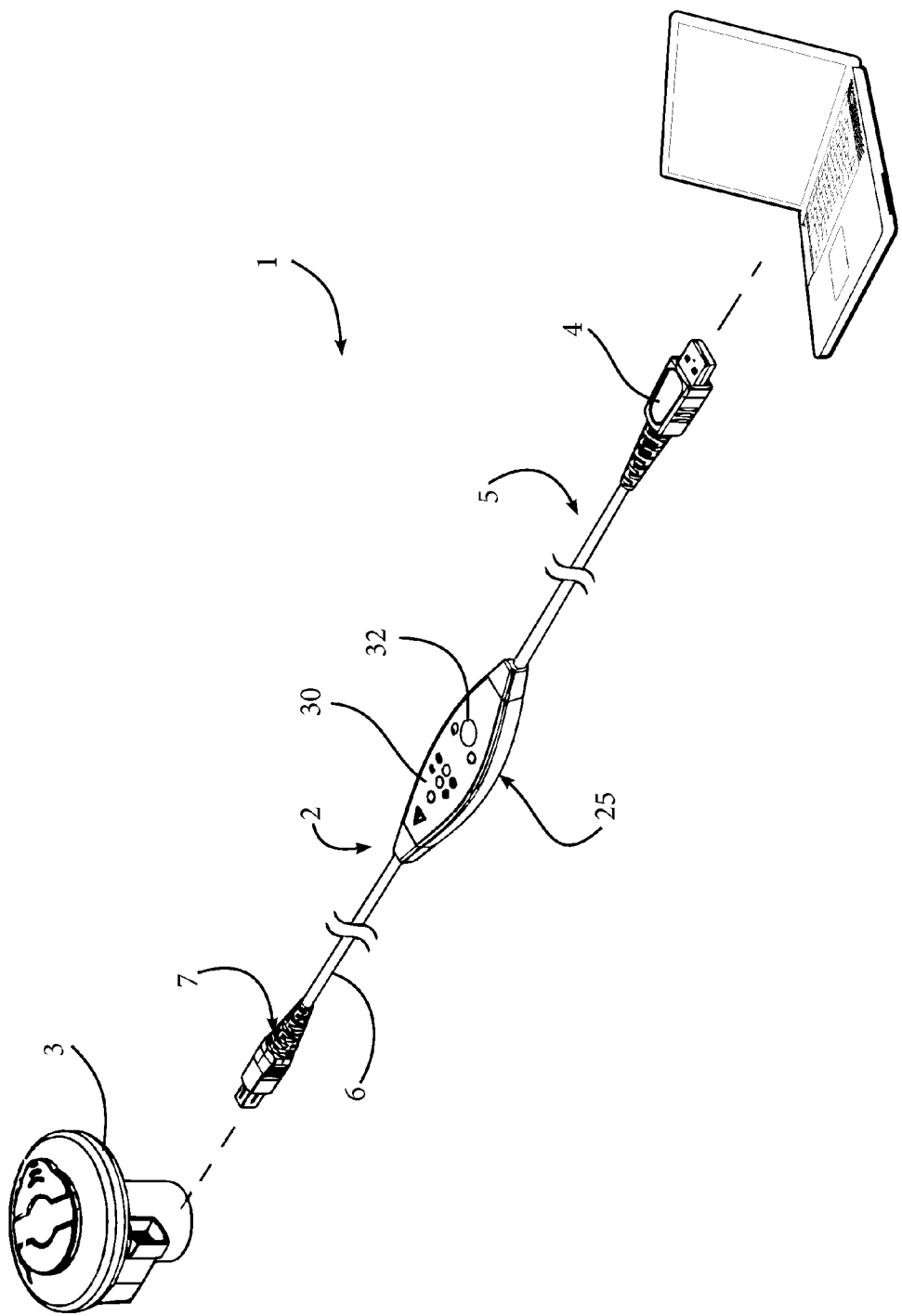
FIG. 2 is a perspective view of the nebulizer.

Referring to the drawings, a nebulizer 1 comprises a controller 2 linked to a vibrating mesh nebulizer head 3. The nebulizer 1 also comprises a USB plug 4 for connection to a host system or device.

The link between the USB plug 4 and the controller 2 is a USB (Universal Serial Bus) cable 5 with power and data channels. The link between the controller 2 and the nebulizer head 3 is a proprietary cable 6 with power and data channels and a proprietary plug 7.

The controller 2 comprises a boost circuit 10 consisting of a custom optimized high frequency, high efficiency DC to DC converter with an integrated power switch capable of providing an output voltage and current profile suitable to drive the nebulizer load, There is also a drive circuit 12 utilizing a series inductor to generate the alternating AC voltage. The drive circuit 12 incorporates a high speed MOSFET driver controlled by a pulse width modulated signal from the microcontroller. There is also a microcontroller 11 with an integrated peripheral module featuring a full speed USB 2.0 compliant interface that can automatically change clock sources and power levels upon connection to a host. The latter provides power and control signals via the cable 6 and the proprietary plug 7 to the nebulizer head 3. These signals provide power and control for a vibrating membrane receiving a liquid to be aerosolised from a feed container. An example of the nebulizer head is described in our previous PCT application WO2012/

046220. The controller 2 and the nebulizer head 3 require no more than 500 mA at nominal 5V to generate a desired aerosol.

The controller 2 has a housing 25 with LED status lamps 30, and an ON/OFF button 32. Communication takes place between the controller 2 and the USB plug 4 in compliance with the USB protocol.

The nebulizer drive circuit 12 consists of components to generate an output sine waveform of approximately 100V AC which is fed to the nebulizer head 3, causing aerosol to be generated. It uses inputs from the microcontroller 11 and the boost circuit 10 to achieve its output. The drive circuit 12 is matched to the impedance of a piezo ceramic element which causes the membrane to vibrate to ensure good energy transfer.

The microcontroller 11 generates a square waveform of 120 to 150 KHz which is sent to the drive circuit 12. The boost circuit 10 generates a nominal 12V DC voltage required by the drive circuit 12 from an input within the range of 4.75V to 5.25 V DC as per USB 2.0 electrical input requirements (released April 2000). The circuit is matched to the impedance of the piezo ceramic element within the nebulizer head 3 to ensure enhanced energy transfer. A drive frequency of 120 to 150 kHz is generated to drive the nebulizer head 3 membrane at close to its resonant frequency so that enough amplitude is generated to break off droplets and produce the aerosol. If this frequency is chopped at a lower frequency such that aerosol is generated for a short time and then stopped for a short time this gives good control of the nebulizer's flow rate. This lower frequency is called the "pulse rate".

The drive frequency may be started and stopped as required using the microcontroller 11. This allows for control of flow rate by driving the nebulizer head 3 for any required pulse rate. The microcontroller 11 may control the ON and OFF times to an accuracy of milliseconds.

The nebulizer head 3 may be calibrated at a certain pulse rate by measuring how long it takes to deliver a known quantity of solution. There is a linear relationship between the pulse rate and the nebulizer flow rate. This may allow for accurate control over the delivery rate of the aqueous solution.

Because of use of the universal bus, in this case the USB cable 5 and the USB plug 4, the controller 2 can achieve very wide-ranging control of the nebulizer head 3. Also, it allows the controller 2 to be connected to a host having data processing and USB communication capability (such as a host computer or a portable device) for upload of information previously captured from the nebulizer head 3, or for download of configuration settings or other data to the controller 2. In combination, the host and the nebulizer 1 form a system which may advantageously be used, for example, for clinical trials or controlled hospital or home treatment regimes.

The controller 2 can upload in various embodiments the following nebulizer characteristics to the host:
 power consumption, and/or
 wet/dry state, and/or
 nebulizer disconnect status, and/or
 cable disconnect status, and/or
 error or fault states, and/or
 nebulization duration and time of nebulization.

The host can in various embodiments provide the following instructions to the controller 2:
 nebulization start/stop, and/or
 nebulization time, and/or
 nebulization flow rate, and/or
 nebulization pulse rate, and/or
 inspiratory/expiratory signal to enable phased nebulization.

This will allow the controller 2 to be controlled via a host, either locally or remotely. The controller 2 may operate as a slave device, with the dosing regime determined by the host. This allows comprehensive control and treatment monitoring for a wide variety of situations such as in the home or in hospitals. If the controller is in communication with an external device, it can then act as a slave device and take commands form the external device. If it is powered by an external device, the mode of operation will be determined by the user input via the ON/OFF (power) button 32 and in this case the controller can be thought of being in "master" mode.

In other embodiments, the controller may be in the form of a hand held device, and may in fact be a mobile phone programmed to generate a user interface for nebulizer control. A specific mobile phone application could be generated to enable control of nebulization.

Figure 3:
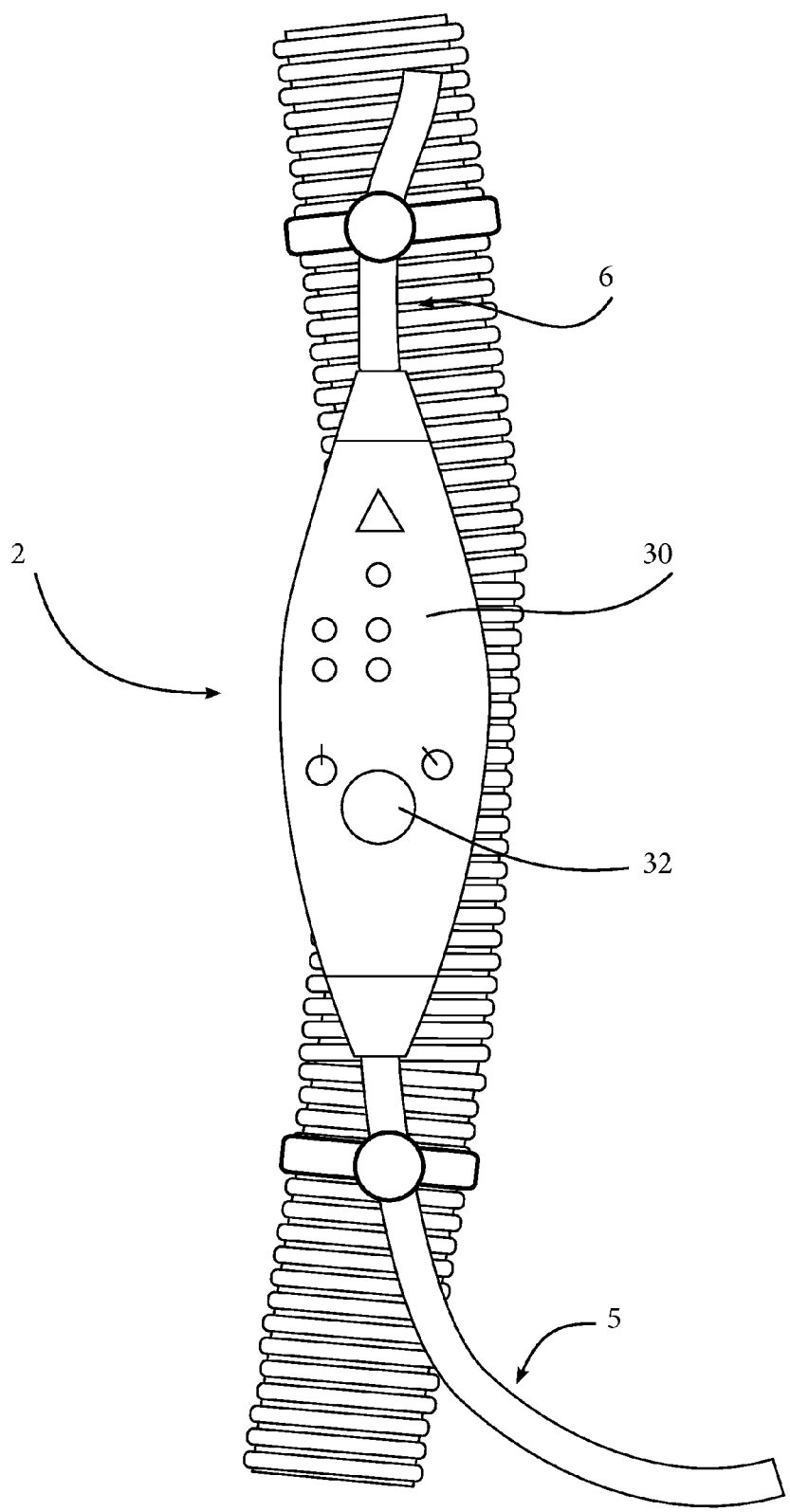
FIG. 3 shows the nebuliser in use in one example with the controller attached to a ventilation tube.

The arrangement of having the USB plug 4, the USB cable 5, the small hand-held controller 2, the cable 6 and the proprietary plug 7 allows convenience and versatility in use. For example, as illustrated in FIG. 3 the cables 5 and 6 along with the controller 2 may be secured by ties to a ventilator tube. However, they may be attached to any other tubular or elongate member. This allows convenience of access by care-givers and patients alike.

It will also be appreciated that the nebuliser can be plugged into any host system. The arrangement gives flexibility in a care-giving setting where there are multiple ventilators and patents. The USB interface allows link-up with a host device to allow remote control by a care-giver, for example, for control over the Internet to a host laptop computer into which the nebuliser is plugged.

Further, the extent of allowable local control may be limited to on/off control by limiting scope of the interface on the controller 2, the dosing control (pulse rate, flow rate, frequency etc.) being controlled from a remote location via a the host system. The controller may execute a program such as an "app" which allows a patient-specific dosing regime to be downloaded from to a mobile/tablet/PDA. The local program will then implement this new dosing regime.

There is excellent versatility because the nebuliser can be used with a ventilator, car socket, laptop computer, desktop computer, or battery pack. Because the controller is essentially part of the cabling it may not be by-passed accidentally.

The following are other benefits which arise from the invention in various embodiments:
 Increased portability due to elimination of need for additional accessories, such as battery packs, AC/DC power adapters. These are eliminated because of the common use of USB ports in general electrical equipment, such as mobile phones, computers, and medical electrical equipment
 Eliminates need for supporting brackets.
 Eliminates need for country-specific power adapters.
 Can be used in remote areas where power is not available, for example, using solar power, hand crank battery pack
 Fewer components.
 Low power consumption.
 Plug and play operation
 Can communicate with a host controller, with ability to collect patient dosing data and communicate it to the host.

Avoidance of need to integrate a control PCB into medical electrical equipment in order to operate from the ME GUI (graphical user interface). For example, it is known at present to integrate an Aerogen™ control PCB into a ventilator, to enable operation of nebulizers via the ventilator interface. The present invention will remove the need for such integration.

Compatibility/usability with wide variety of medical electrical equipment (i.e. any equipment with USB port).

Can be powered by any of a range of devices such as USB battery packs or portable solar panels.

The controller may be hand-held having a battery and power supply akin to that of a mobile phone.

The invention is not limited to the embodiments described but may be varied in construction and detail.

The invention claimed is:

1. A nebulizer comprising a nebulizer head for generating an aerosol, a controller for delivering power and control signals to the head, and a standard universal bus for delivering power and control signals to the controller, wherein the standard universal bus comprises a universal plug and a universal cable extending from said universal plug to the controller, wherein the controller is linked by a head cable and a head plug to the head;

wherein the controller comprises a voltage boost circuit linked at its input with the universal bus, a processor, and a drive circuit for delivering power to the nebulizer head under control of the processor according to said power and control signals delivered to the controller via the standard universal bus;
wherein the controller is configured to receive one or more of the following signals from a host via the universal bus and to use the one or more signals to generate nebulizer head drive signals:

a nebulization start/stop signal, a nebulization time signal, a nebulization flow rate signal, a nebulization pulse rate signal, and an inspiratory/expiratory signal to enable phased nebulization; and wherein the processor is configured to upload to the host via the universal bus the following nebulizer characteristic information previously captured from the nebulizer head:

a wet/dry state of the nebulizer head, a nebulizer disconnect status, a cable disconnect status, an error or fault status, and a nebulization duration and time of nebulization.

2. The nebulizer as claimed in claim 1, wherein the universal bus is a USB bus, and wherein a total power requirement of the controller and of the nebulizer head falls within a power specification of USB protocol.

3. The nebulizer as claimed in claim 1, wherein the universal bus is a USB bus, and wherein a total power requirement of the controller and of the nebulizer head falls within a power specification of USB protocol; and wherein the controller provides to the nebulizer head no more than 500 mA at nominal 5V.

4. The nebulizer as claimed in claim 1, wherein the drive circuit is adapted to generate a waveform having a frequency range between 120 kHz and 150 kHz.

5. The nebulizer as claimed in claim 1, wherein the boost circuit is adapted to generate a voltage supply for the processor and the drive circuit.

6. The nebulizer as claimed in claim 1, wherein the boost circuit is adapted to generate a voltage supply for the processor and the drive circuit; and wherein a voltage level of the voltage supply is 12V.

7. A nebulizer system comprising:

a nebulizer comprising:

a nebulizer head for generating an aerosol, a controller for delivering power and control signals to the head, a processor of the controller, and a bus for delivering power and control signals to the controller, wherein the bus comprises a bus plug and a bus cable extending from said bus plug to the controller, wherein the controller is linked by a head cable and a head plug to the head; and a host system adapted to provide control signals to the controller via said bus, wherein the controller has a longitudinal length extending between a first end and a second end opposite the first end, wherein the head cable, controller, and bus cable form an in-line arrangement, wherein the head cable extends from the first end towards the head plug, and wherein the bus cable extends from the second end towards the bus plug, wherein the head plug is proprietary to the head and the bus plug is a standard universal bus plug;

wherein the controller is configured to receive one or more of the following signals from the host system via the universal bus and to use the one or more signals to generate nebulizer head drive signals:

a nebulization start/stop signal, a nebulization time signal, a nebulization flow rate signal, a nebulization pulse rate signal, and an inspiratory/expiratory signal to enable phased nebulization; and wherein the processor is configured to upload to the host system via the universal bus the following nebulizer characteristic information previously captured from the nebulizer head:

a wet/dry state of the nebulizer head, a nebulizer disconnect status, a cable disconnect status, an error or fault status, and a nebulization duration and time of nebulization.

8. The system as claimed in claim 7, wherein the host system is adapted to provide the control signals according to a patient dosing regime.

9. The system as claimed in claim 7, wherein the host system includes a component adapted to communicate with a remote server for download of control instructions and/or upload of nebulizer data.

10. The system as claimed in claim 7, wherein the host system includes at least one of a smartphone or tablet computer.

11. A nebulizer, comprising:

a nebulizer head;

a controller having a longitudinal length extending between a first end and a second end opposite the first end, wherein the controller includes a voltage boost circuit, a processor, and a drive circuit; and a bus;

wherein the controller is coupled to the head via a head cable extending from the first end of the controller, and wherein the controller is coupled to the bus via a bus cable extending from the second end of the controller, wherein the head cable, controller, and bus cable form an in-line arrangement; and wherein the bus is a universal bus and the controller is interchangeably coupleable to a plurality of host systems of varying configurations and/or functions via the bus;

wherein the controller is configured to receive one or more of the following signals from at least one of the plurality of host systems via the universal bus and to use the one or more signals to generate nebulizer head drive signals:

a nebulization start/stop signal, a nebulization time signal, a nebulization flow rate signal, a nebulization pulse rate signal, and an inspiratory/expiratory signal to enable phased nebulization; and wherein the processor is configured to upload to the at least one of the plurality of host systems via the universal bus the following nebulizer characteristic information previously captured from the nebulizer head:

a wet/dry state of the nebulizer head, a nebulizer disconnect status, a cable disconnect status, an error or fault status, and a nebulization duration and time of nebulization.

12. The nebulizer as claimed in claim 11, further including a head plug coupled to the head cable.

13. The nebulizer as claimed in claim 12, wherein the head is selectively coupleable and uncoupleable from the controller via the head plug.

14. The nebulizer as claimed in claim 12, wherein the head plug is received within a head port on the head.

15. The nebulizer as claimed in claim 11, further including a bus plug coupled to the bus cable.

16. The nebulizer as claimed in claim 11, wherein the at least one of the plurality of host systems includes at least one of a smartphone or tablet computer.

17. The nebulizer as claimed in claim 11, wherein the controller includes an ON/OFF button and a plurality of LED status lamps.

* * * * *